(12) United States Patent
Perry

(10) Patent No.: US 6,982,763 B2
(45) Date of Patent: Jan. 3, 2006

(54) VIDEO STANDARDS CONVERTER

(75) Inventor: John R. Perry, West Jordan, UT (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 570 days.

(21) Appl. No.: 09/920,391

(22) Filed: Aug. 1, 2001

(65) Prior Publication Data

US 2003/0025830 A1 Feb. 6, 2003

(51) Int. Cl.
*H04N 3/27* (2006.01)
*H04N 5/46* (2006.01)

(52) U.S. Cl. ..................................... 348/441

(58) Field of Classification Search ............... 348/441, 348/443, 445, 446, 448, 449, 455, 458, 459, 348/554, 556, 558, 588, 705–706; 345/1.1, 345/1.2, 3.1; 710/100
See application file for complete search history.

(56) References Cited

U.S. PATENT DOCUMENTS

| | | | | |
|---|---|---|---|---|
| 4,018,990 A | * | 4/1977 | Long et al. .................. | 348/513 |
| 4,053,946 A | * | 10/1977 | Opittek et al. ............... | 345/501 |
| 4,525,836 A | * | 6/1985 | Dayton et al. ............... | 370/362 |
| 4,791,489 A | * | 12/1988 | Polatnick .................... | 348/578 |
| 4,956,707 A | * | 9/1990 | Oakley et al. ............... | 348/441 |
| 5,012,337 A | * | 4/1991 | Gillard ....................... | 348/452 |
| 5,068,850 A | * | 11/1991 | Moore ........................ | 370/449 |
| 5,367,331 A | * | 11/1994 | Secher et al. ............. | 348/14.01 |
| 5,552,807 A | * | 9/1996 | Hayes et al. ................ | 345/156 |
| 5,694,141 A | * | 12/1997 | Chee .......................... | 345/3.1 |
| 5,768,612 A | * | 6/1998 | Nelson ....................... | 712/32 |
| 5,790,096 A | * | 8/1998 | Hill, Jr. ...................... | 345/600 |
| 5,812,801 A | * | 9/1998 | Saperstein et al. .......... | 710/305 |
| 6,023,252 A | * | 2/2000 | Yano et al. .................. | 345/1.1 |
| 6,061,754 A | * | 5/2000 | Cepulis et al. .............. | 710/312 |
| 6,297,785 B1 | * | 10/2001 | Sommer et al. ............. | 345/1.1 |
| 6,333,750 B1 | * | 12/2001 | Odryna et al. .............. | 345/629 |
| 6,388,658 B1 | * | 5/2002 | Ahern et al. ................ | 345/168 |

* cited by examiner

*Primary Examiner*—Paulos M. Natnael
(74) *Attorney, Agent, or Firm*—McAndrews, Held & Malloy, Ltd.; Peter J. Vogel; Michael A. Dellapenna

(57) ABSTRACT

A video standards converter (VSC) has a first input module, a second input module, a bus attached to the first and second input modules, a first output module attached to the bus and having a first video standard, and a second output module attached to the bus and having a second video standard. The first and second video standards may be different. The first input module may be adapted to convert an analog video signal to a digital signal. The second input module may be adapted to convert an analog video signal to a digital signal. The VSC may include a picture-in-picture feature for displaying images from two different sources simultaneously. The VSC may be employed in methods for converting a signal from a first video standard to a second video standard.

26 Claims, 6 Drawing Sheets

VIDEO STANDARDS CONVERTER

BACKGROUND

The present invention is directed to video standards converters. More particularly, the present invention is directed to video standards converters for converting standards of video devices employed in connection with the medical field.

Urology suites typically contain two or more devices, such as a monochrome X-ray system or a color endoscope, for displaying video images. Often, the devices operate at different frequencies (or "standards") and thus provide video sources at different standards. Standards include NTSC/PAL, computer video (VESA standards) as well as proprietary scanning frequencies and resolutions. Conventional video standards converters (VSCs) are devices that convert a single video input to a single video output. Because conventional VSCs convert only a single video input, conventional VSCs are not capable of reducing the number of video display devices employed in a urology suite or in another system with multiple video sources.

In conventional medical systems, when multiple video sources are employed that have different standards, multiple display devices are needed for a physician to be able to view the video sources. The functionality of a urology suite, however, suffers when urologists need to view more than one monitor simultaneously. There is a need to reduce the total number of monitors in order to provide improved functionality.

To improve urology suite functionality, it is desirable to reduce the number of monitors while providing quality video from several sources. Typically, equipment designed with an external video input requires inputs or sources with matching video standards. For example, an NTSC endoscope with external video input requires the external video source to be NTSC. However, the other source to be used with the video display of the endoscope may be capable of far superior video scan rates and resolution than NTSC. Thus, there is a need to accommodate multiple video sources without significantly compromising the quality of the video sources when displayed.

BRIEF SUMMARY OF THE INVENTION

In accordance with at least one embodiment of the present invention, a video standards converter (VSC) is provided that includes a first input module, a second input module, a bus attached to the first and second input modules, a first output module attached to the bus and having a first video standard, and a second output module attached to the bus and having a second video standard. The first and second video standards may be different. The first input module converts an analog video signal to a digital signal, and the second input module converts an analog video signal to a digital signal. The VSC may comprise one or more of the following: additional input modules, additional output modules, a dual-input module, and a dual-output module. The first and second video standards may be selected from the group comprising OEC Hi-Res monochrome, Dual NTSC/PAL S-Video, VESA computer video, and HDTV.

A further embodiment of a VSC in accordance with the present invention includes a first input module having a first video standard, a second input module having a second video standard, a bus attached to the first and second input modules and having a third video standard, a first output module attached to the bus and having a fourth video standard, and a second output module attached to the bus and having a fifth video standard. The first input module converts a video signal from the first video standard to the third video standard. The second input module converts a video signal from the second video standard to the third video standard, and the fourth video standard is different from the fifth video standard.

Another embodiment of the present invention includes a system for converting video standards. The system includes a first input module adapted to receive an analog video signal from a first video source and adapted to convert the analog video signal to a digital video signal, a second input module adapted to receive an analog video signal from a second video source and adapted to convert the analog video signal to a digital video signal. A bus is attached to the first and second input modules, and an input selection and control device (ISC) is included for selecting at least one of the first and second input modules to drive the bus. The embodiment also includes a computer for controlling the ISC, first and second output modules attached to the bus, a first video device attached to the first output module, and a second video device attached to the second output module. The first output module converts a standard of a video signal from a bus standard to a standard of the first video device. A video standard of the first output module is different from a video standard of the second output module. The first and second video devices have different standards.

Still another embodiment of the present invention comprises a system for displaying images from two sources. The system comprises a first input module, a second input module, a bus attached to the first and second input modules, a first output module attached to the bus, a second output module attached to the bus, and a first display device attached to one of the first and second output modules. The first input module converts a first analog video signal to a first digital video signal. The second input module converts a second analog video signal to a second digital video signal. The bus drives the output modules to convert the first and second digital video signals to respective first and second analog display signals containing images for reception by the first display device. At least a portion of each image from the first and second analog display signals are displayed on the first display device. Images from one of the first and second analog display signals may be displayed in a quadrant of the first display device. Padding may be positioned adjacent at least a portion of the images from the first or second analog video display signals. The system may comprise an ISC for selecting one of the first and second video signals to be a window image and the other video signal to be the background image. The system may comprise a second display device, the first display device being attached to the first output module, the second display device being attached to the second output module, and the first and second display devices having different standards.

Another aspect of the present invention is a method for converting a plurality of video sources having different standards. Yet another aspect of the present invention is a method of displaying images from two sources. The method of displaying images from two sources comprises the steps of: providing a video standards converter comprising a first input module connected to a first source, a second input module connected to a second source, a bus attached to the first and second input modules, a first output module attached to the bus, a second output module attached to the bus, and an input selection and control (ISC) in communication with the input modules.

Further steps include providing a display device connected to one of the output modules, employing the first input module to convert a video signal of the first source from analog to digital, employing the second input module to convert a video signal of the second source from analog to digital, and employing the bus to drive the first and second output modules to convert the video signals from digital to analog. A step of positioning images from the first and second sources on the display device may also be performed. The step of positioning images may minimize any overlap of the images of the first source and the images of the second source. The step of positioning images may comprise the step of selecting a quadrant of the display device in which to position the images of one of the sources. The step of positioning images may comprise positioning the images of one of the first and second sources in a quadrant containing a corner of the display device that is farthest from a corner of the display device contained in the quadrant selected for positioning the images of the other source.

BRIEF DESCRIPTION OF THE DRAWINGS

The foregoing summary, as well as the following detailed description of the preferred embodiments of the present invention, will be better understood when read in conjunction with the appended drawings. For the purpose of illustrating the preferred embodiments of the present invention, there is shown in the drawings, embodiments which are presently preferred. It should be understood, however, that the present invention is not limited to the arrangements and instrumentality shown in the attached drawings.

DETAILED DESCRIPTION OF THE INVENTION

Figure 1:
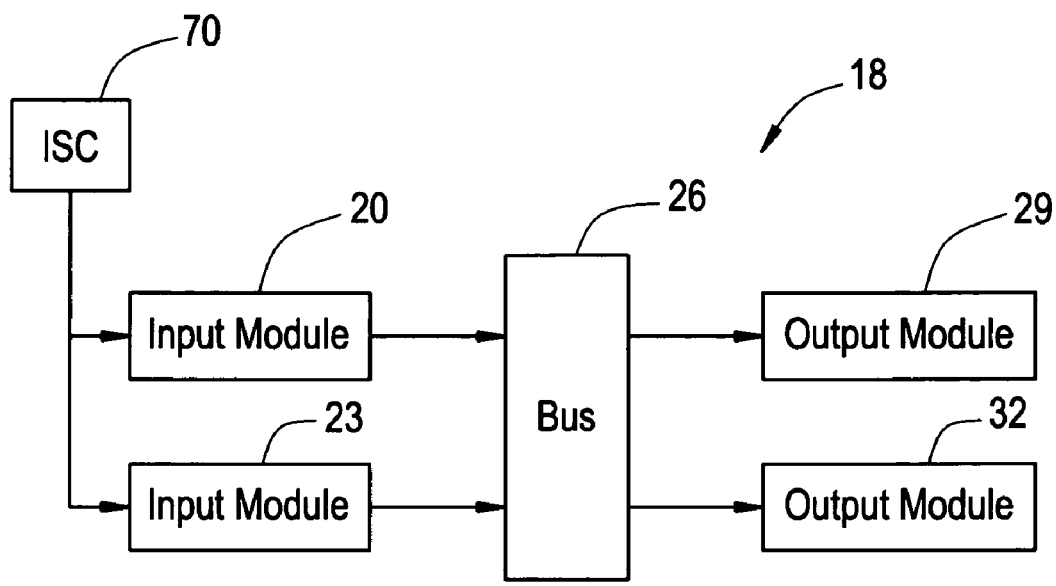
FIG. 1 is a block diagram of a video standards converter in accordance with an embodiment of the present invention.

A video standards converter (VSC) 18 formed in accordance with one embodiment of the present invention is shown in FIG. 1 and comprises a first input module 20 having a first video standard, a second input module 23 having a second video standard, and a bus 26 attached to the first and second input modules 20, 23. The video standard of the bus 26 is a third video standard. The first and second video standards may be the same or different. Additionally or alternatively, the third video standard may be the same as one or both of the first and second video standards.

The first and second output modules 29, 32 are attached to the bus 26 and have a fourth and fifth video standard, which may or may not be the same as the third video standard. One of the first and second input modules 20, 23 converts a video signal from the first video standard to the third video standard. The output modules 29, 32 are driven by the bus 26 for converting the video signal to the fourth and fifth video standards.

Figure 4:
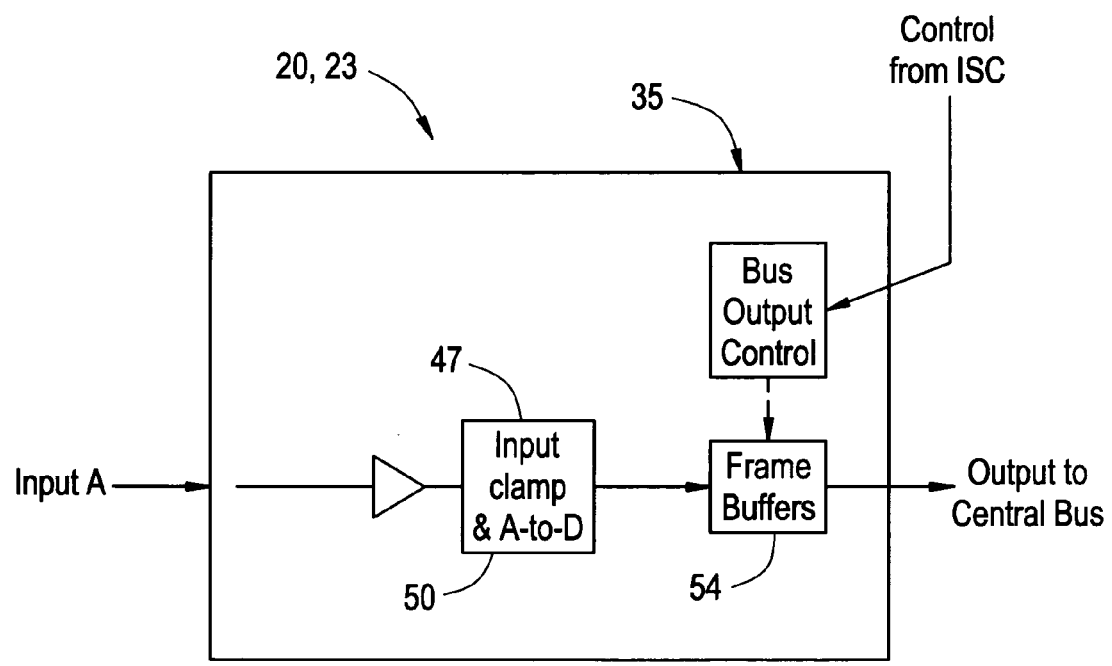
FIG. 4 is a schematic of an embodiment of an input module.
Figure 5:
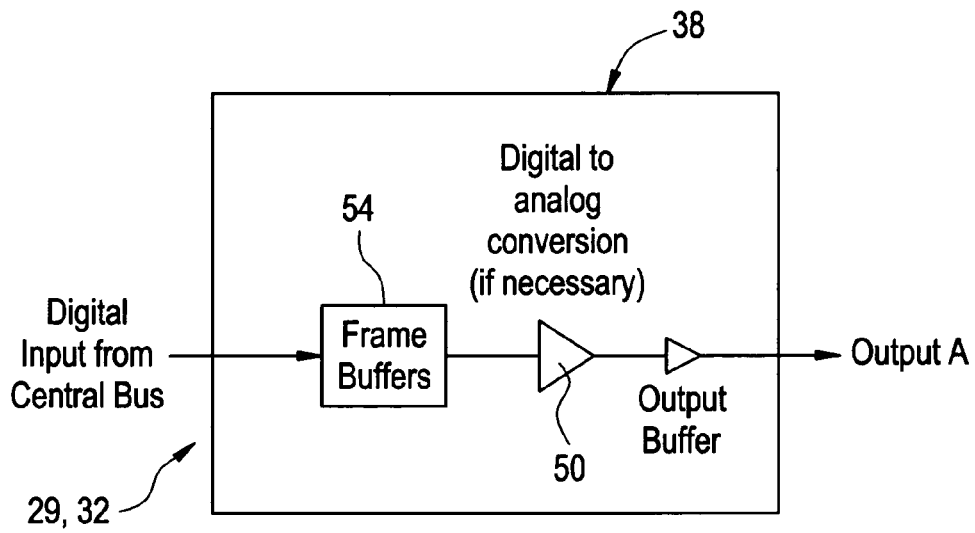
FIG. 5 is a schematic of an embodiment of an output module.

The first and second input modules 20, 23, are shown in greatest detail in FIG. 4, each comprising a video input board 35 or card. The first and second input modules 20, 23 may be attached to the bus 26 through a plug connection. The first and second output modules 29, 32, shown in greatest detail in FIG. 5, comprise a video output board 38 or card and may be attached to the bus 26 by being plugged into the bus 26. Input sources 41 that supply the original video signal or signals may be plugged into the input modules 20, 23. In the embodiment of FIG. 1, each input module 20, 23 is adapted to receive only a single input source 41.

The video input sources 41 each are capable of providing an input video signal. Each input module 20, 23 synchronizes the input signal that it receives with the timing of the bus 26 and converts the input signal to the frequency of the bus 26 prior to placement on the bus 26. The input modules 20, 23 comprise an input clamp 47 that sets the video blanking to ground. The input modules 20, 23 also comprise an analog-to-digital converter 50.

Conversion and synchronization occur by the use of frame buffers 54. Each input module 20, 23 comprises a dual frame buffer 54 having an input frame buffer (not shown) and an output frame buffer (not shown). An incoming video signal from a source attached to the input module is converted by being sampled and captured in the input frame buffer. The output frame buffer places the converted signal on the bus 26. The input and output frame buffers switch roles after one set of converted signal data has been placed on the bus 26. Thus, the input and output buffers alternate between capturing data from the incoming video signal and placing the converted signal on the bus 26. In this fashion, the input and output frame buffers fill the bus 26 with signal data that has the same frequency as the bus 26. The bus 26 times how the data is pulled off of the output frame buffer or buffers which make the input signal or signals synchronous prior to being placed onto the bus 26.

The output board or boards 38, which may be plugged into the bus 26, convert the video signal from the bus 26 frequency to the frequency of the output module. Each output module 29, 32 or board 38 is dedicated to a frequency, a frequency that equals the standard of the device or devices that are to be attached to the output module.

It is preferred that the bus 26 have a bandwidth capable of handling the highest frequency video input or output. In such an embodiment, the bus 26 can drive any of the output modules 29, 32 to which it is attached and the bus 26 does not limit output speed. The bus 26, however, may have a lower frequency than one or more of the output modules 29, 32.

The bus 26 uses wide-parallelism to achieve the necessary bandwidth. Red, green and blue color channels are provided on the bus 26. Wide buses 26 in parallel are employed to achieve the necessary bandwidth for up to 75 hz output refresh rates. The bus 26, in part, may be described as being analogous to a video screen because the bus 26 has a particular resolution and frequency associated with it.

Each input module converts input video to digital video that is synchronous with bus video and positions the video in bus video. Many output video devices 66 are analog, so the digital signal from the bus 26 is converted into analog for analog video devices 66. There are some output video devices 66, such as output video devices 66 operating using DICOM or digital video, that could be sent a signal from the bus 26 without the output module having to convert the signal to analog. If an output module 29, 32 has to convert to analog, the conversion is performed in accordance with the standard of the output video device 66.

Figure 2:
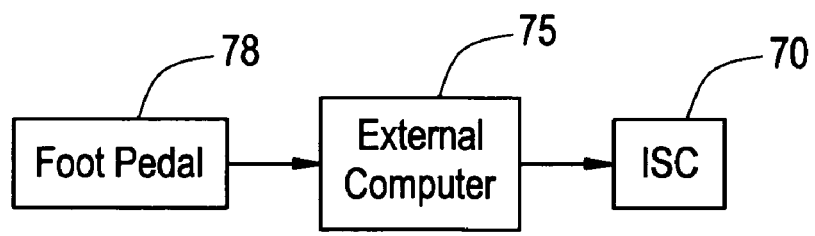
FIG. 2 is a block diagram of features for controlling the ISC.

An Input Selection and Control (ISC) box 70 controls data that is placed on the bus 26 by the input modules 20, 23. The ISC box 70 has registers to determine some of the parameters of the input modules 20, 23. Registers hold the settings for image parameters such as height and width and position of input source video image, and the registers also control placement of the image on the bus 26. An external computer 75 (FIGS. 2 and 3) may be employed to drive the ISC box 70 and to act as a user interface. A foot-pedal 78 (FIG. 2) or other suitable device connected to the computer 75 may be used by an operator to control the computer 75 and change the registers. The registers may have default settings so that the registers have the appropriate resolution and frequency for the particular bus 26 that is being employed. Position on the bus 26 corresponds to video placement on a video display 66 having the same standard as the bus 26.

Each output module 29, 32 attaches to the bus 26 and converts high-bandwidth bus video into the specified output video format, e.g. SXGA (or other VESA standards), NTSC/PAL, digital video, etc. The conversion process is similar to the conversion process performed by the input modules 20, 23 when converting a signal to the standard of the bus 26 by using input and output frame buffers. The output module 29 or 32 is matched to the standard of the connected equipment. The equipment may be a video device 66, where video device is a general term encompassing video display devices, VCRs, DVRs (digital video recorders) or DICOM. The term video display device does not include VCRs but does include monitors, televisions, and flat screen displays, among other things. A function of an SXGA output module, for example, is to convert wide parallel data into red, green, blue analog-video at SXGA rates. Thus the SXGA output module performs digital-to-analog conversion but no frequency conversion because the bus operates at SXGA rates.

The video on the bus 26 simultaneously drives all output modules 29, 32. Therefore, the output modules 29, 32 receive the same image. All of the output display devices display the same video image, but in the video format and standard defined by the particular output module 29, 32 to which each output display device 66 is attached.

The bus 26 could be designed to operate at any frequency standard. SXGA is a common standard for use with flat panel displays. In embodiments in which the bus 26 runs at the SXGA rate, video inputs and/or outputs operating at SXGA rates require no scaling and avoid the associated probability of conversion artifacts. In general, if the bus 26 frequency matches the frequency of either the video source or the output device 66, then there will be fewer artifacts and loss than if conversion was needed on both sides. As technology and video scan rates increase, higher bandwidth bus rates may be necessary, although the input and output modules 29, 32 may not have to be changed significantly.

In one embodiment, at least one output module 29, 32 is a dual-output module 85 having two output connectors 87. The dual-output module 85 makes it possible to send the output to two devices 66 having the same standard. For example, a monitor and a VCR having the same standard could be connected to the same dual-output module 85 without the need for distribution amplifiers or looping video.

Figure 3:
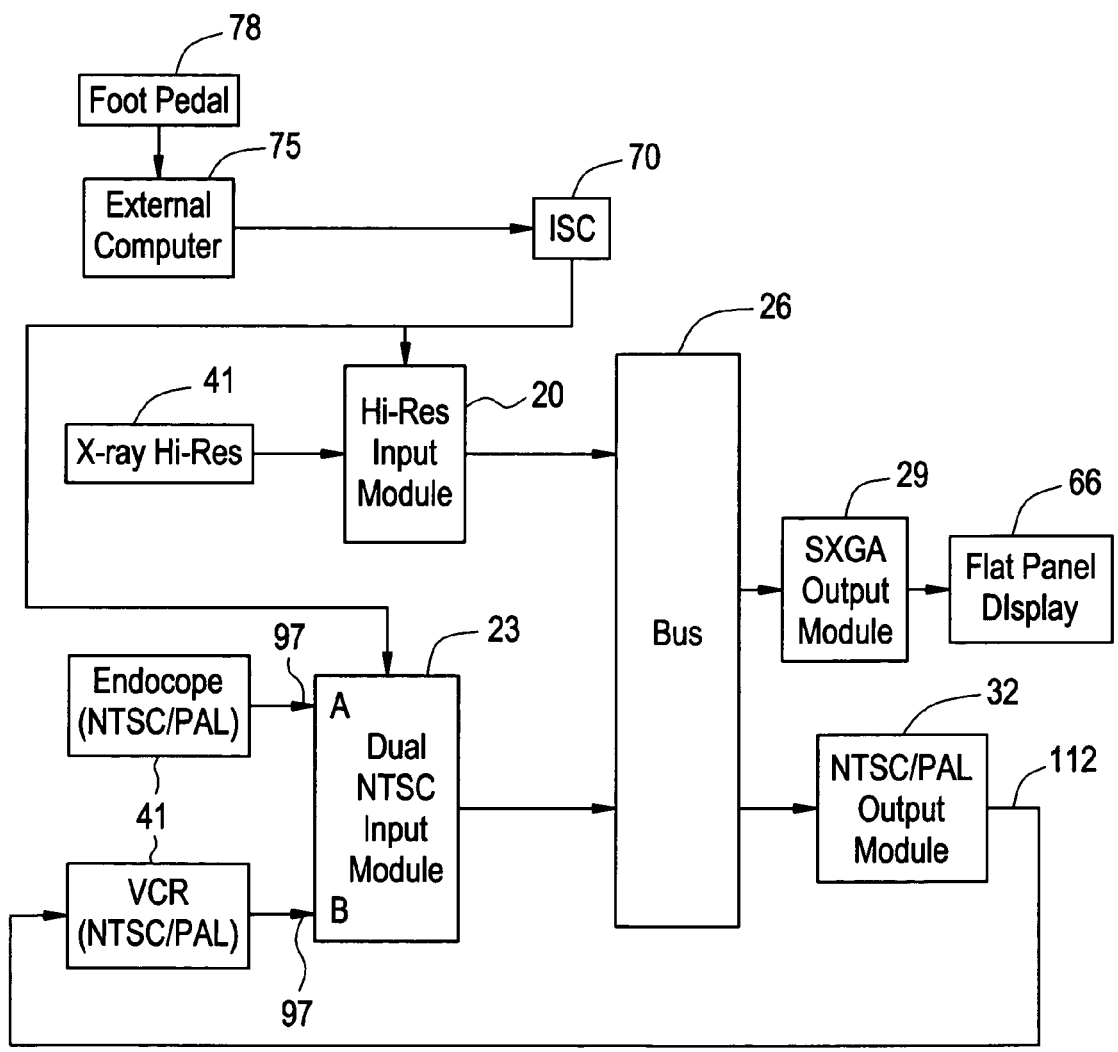
FIG. 3 is a block diagram of a system of converting video standards in accordance with an aspect of the present invention having a dual-input module.
Figure 6:
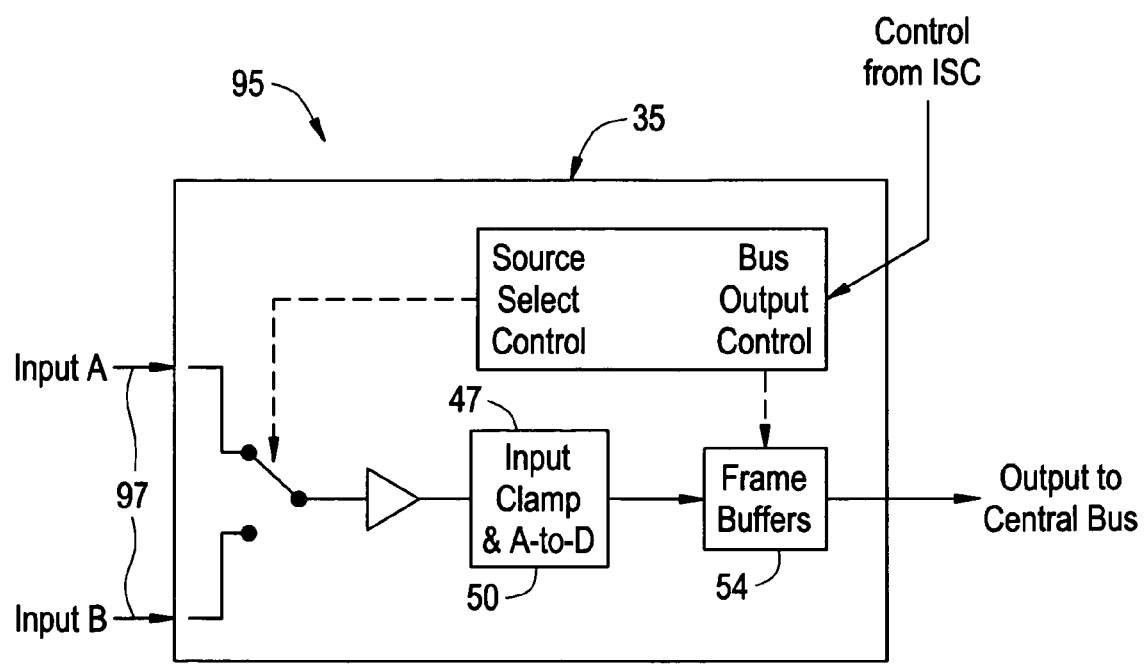
FIG. 6 is a schematic of an embodiment of a dual-input module.
Figure 7:
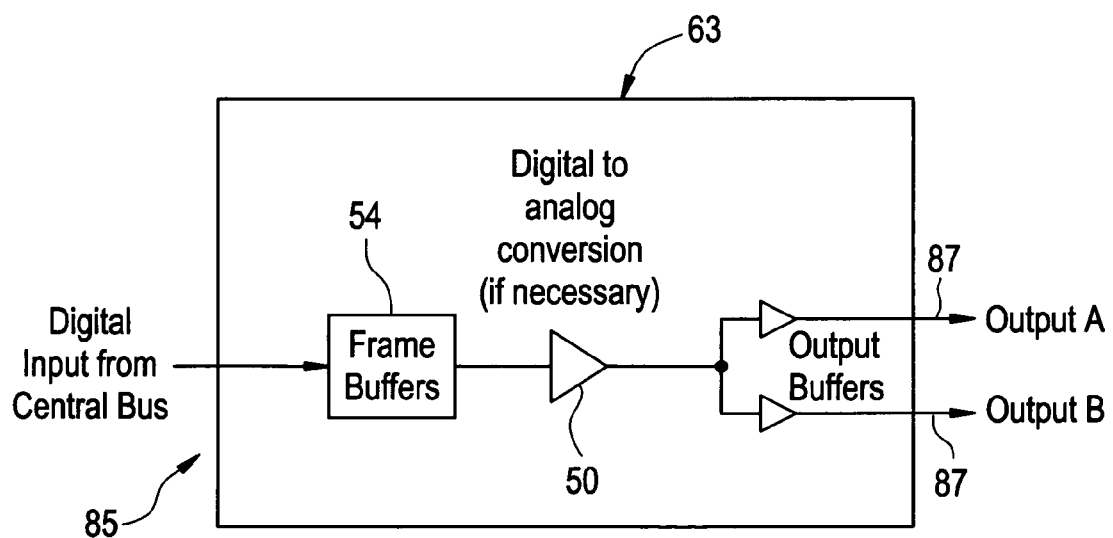
FIG. 7 is a schematic of an embodiment of a dual-output module.

In some alternative embodiments, such as the embodiment shown in FIG. 3, one or more input modules 20, 23 may have dual inputs. A dual-input module 95 is shown in greater detail in FIG. 6. Both inputs 97 of a dual-input module 95 have identical video standards, such as NTSC. The video sources are switched at the input to the dual-input module 95 prior to bus processing. Therefore, the two inputs 97 of a dual-input module 95 cannot be displayed simultaneously by picture-in-picture (PIP). Dual-input modules 95 may be desirable where it is known that two video sources with identical standards need to be displayed but not at the same time. For example, it may not be desirable to play back VCR video while observing endoscope video on the same monitor (e.g., by using PIP). Therefore, a VCR and an endoscope could be connected to the same dual-input module 95. For example, an S-video input module could use a dual-input module NTSC standard for a VCR and an endoscope. An example of a dual-input module is a dual S-Video input at NTSC/PAL frequencies. The dual input reduces component complexity and cost by allowing two input sources to be converted by a single board 35 rather than two boards 35. In this way, duplication of board components such as a sync separator, chroma decoder, PLL and scan converter (not shown, but those four board components are part of the Input Clamp and A-to-D box in FIG. 4) is not necessary to accommodate two input sources of the same standard.

During operation, an operator controls the ISC 70 with the computer 75 or foot-pedal 78 to determine which input module or modules will place video on the bus 26 at any given time. Thus, an operator such as a physician may switch which video signal input (e.g., X-ray, endoscope or VCR) will be displayed simply by using the foot-pedal 78 or otherwise accessing the computer. The ISC 70 controls the video inputs, regardless of video standard, so that the various video inputs are synchronous and positioned as desired at the input to the bus 26. If, for example, a system had three input sources 41 but only one display device 66, an operator would control the ISC 70 to select which input source 41 would be displayed. Also, the doctor can turn picture-in-picture (PIP) on and off during operation. PIP is discussed in detail further below. The selection of a different input video source or turning PIP on and off are changes which alter the registers in the ISC box 70. Either serial (RS422) or parallel port interfaces may be used for selecting input sources, turning PIP on/off, and other PIP aspects described below. The parallel port interface comprises a set of switches that may be used instead of the computer 75. The ISC box 70 may be constructed as part of the bus board.

If a dual S-Video Input Module is used as the input module, the clock phase and image positioning of incoming video for both inputs 97 may be defined by means of serial port communications. Clock phase and image positioning data and any other data required to define each video input may be held in the registers until such time as re-programmed by the external computer 75. If a Computer Video Input Module (VESA) is used as the input module, the frequency, mode, clock phase, image positioning and filtering coefficients of incoming video may be defined by means of serial port communications. The frequency, mode, clock phase, image positioning and filtering coefficients of incoming video and any other data required to define a video input may be held in registers until such time as re-programmed by the external computer 75.

The serial I/O port may have the capability of programming various functions within the system (e.g., image positioning and programming filter coefficients). The parallel port mode may not have programming capability, but has source selection, PIP on/off and quadrant selection control.

Registers are programmed for the system configuration using a serial port (i.e., computer) to set up defaults. Then, if a parallel port is used on the VSC but it is desired to change the resisters, a computer 75 would have to be connected to the registers again to change them.

The parallel port may be implemented so that if all input sources 41 are inactive (e.g., control cables are disconnected), there is a default video that is displayed. The ISC 70 can determine if a video signal is present at an input module 20 or 23. If the operator selects an input source 41 where no video is present (e.g., a video source that is off), the input module will automatically produce a middle-gray video signal. After conversion onto and off of the bus 26, the output video will appear gray rather than black. Thus, when an operator sees a middle-gray video output, the operator will know that the video source is off. If solid black appears as the output video, the black results from an input source that is on but that is producing black output. For example, if the source is an endoscope, a black output would be produced when the light bulb of the endoscope is burned out. Gray indicates to an operator that the source is actually off (no video). If an input source 41 is off and gray is shown on the display, then when the input source 41 becomes active, the gray will disappear and the input source will be displayed.

Another embodiment of the present invention is shown in FIG. 3 and comprises a plurality of input modules 20, 23 and a plurality of output modules 29, 32. A different video source is connected to each input module. The video sources shown in FIG. 3 are part of a urology suite and include an X-ray system as the input source 41 that generates high-resolution monochrome video, an endoscope as the input source 41 generating NTSC,/PAL, and a VCR (NTSC/PAL) as an input source 41 to perform record and playback procedures. In the system shown in FIG. 3, the VSC 18 is connected to an output display device 66 that is a high-resolution color monitor (a flat panel display) and an NTSC output 112 to feed the VCR record inputs. Some embodiments of the present invention, such as the embodiment of FIG. 3, are well suited for use in urology suites, however, other embodiments comprising a plurality of input modules 20, 23 and a plurality of output modules 29, 32 are suitable for other uses as well.

Because of conversion, multiple video sources having different standards may be displayed using a single video display. The VSC 18 eliminates the need for multiple monitors within the urology suite under some situations, because one monitor can display the video content of different sources having different standards, although unless picture-in-picture PIP (discussed below) is operating, only one source is displayed at a time on a single output display device 66. By reducing the number of monitors required, some VSC embodiments of the present invention save space and money. Additionally, some VSC embodiments of the present invention improve urology suite efficiency by saving the urologist's time by allowing the urologist to look at a single screen to see two images rather than two screens.

In some embodiments, such as the embodiment of FIGS. 1 and 3, the VSC 18 has the capability of converting a video input signal into multiple video output standards. Embodiments with multiple input capability and only single output capability may be useful where the customer is viewing the output on a monitor but is not also using a VCR. VSC embodiments having only a single output module as well as VSC embodiments having multiple output modules 29, 32 permit a single monitor to be employed to view video images coming from sources having different video standards.

A maximum of two input modules 20, 23 drive the bus 26 at one time. The ISC 70 may be used to select which module or which two modules drive the bus 26. One VSC embodiment comprises one fixed input module and one fixed output module. The fixed input and output modules 29, 32 are dedicated to particular standards. Other modules attached to the bus 26 can be either input modules 20, 23 or output modules 29, 32 depending on the modules.

When converting from one standard to another, there is a risk of loss of some detail, whether converting from high resolution to low resolution or the other way around. Thus, the frequency of the bus 26 may be selected to minimize the amount of frequency conversion that occurs. If the bus 26 is the same frequency as the output frequency then there will be no artifacts. If, for example, SXGA is the frequency of one of the input sources and one of the output displays, as well as the highest frequency in a given system, then SXGA is a suitable bus frequency for minimizing the amount of frequency conversion that is needed. The SXGA input signal frequency will not have to be converted in order to be displayed on an SXGA display device attached to an output module 29, 32, but the input signal will have to be made synchronous with other sources (if any) when being placed on the bus 26. The output frame buffer automatically makes the signals synchronous.

Most input signals are analog and go through analog-to-digital conversion when being placed on the bus 26. Inherent in that conversion process is some loss of detail, but generally a small amount of loss.

In a further aspect of some embodiments of the present invention, at least one input module horizontally and vertically positions the video image from the source. If necessary, the input module also scales and filters the source video. Filtering may be performed by using filter coefficients on a computer input module (VGA input module) which is a type of input module capable of filtering to minimize artifacts during the frequency conversion process.

Horizontal and vertical positioning may be necessary to compensate for differences in video aspect ratios between the source video and the aspect ratio of the standard used for the bus 26. The aspect ratio is the ratio of width in terms of pixels to the height in terms of scan lines. In SXGA, for example, the aspect ratio is 1.25, because the width is 1280 pixels long and the height is 1024 scan lines. In medical applications it may be undesirable to change the aspect ratio of the source image because the displayed image would be distorted, which might have diagnostic consequences.

In some embodiments of the present invention, when the aspect ratio of the input video source is different from the aspect ratio of the bus 26, then the input module scales the input video. Scaling down is performed until both the length and the width of the input video image fit within the bus 26. The aspect ratio of the input video source is retained. Thus, there may be some blank space along either the width or the height when the scaled input image is placed on the bus 26. The blank space may be padded with black or another color or shade.

Figure 8:
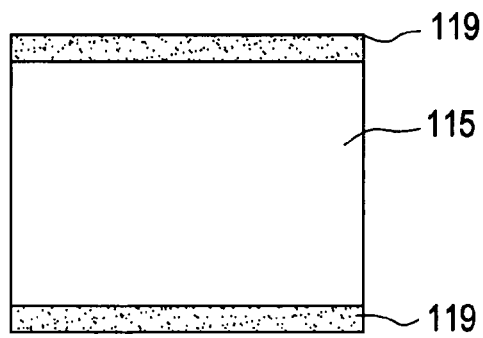
FIG. 8 is a schematic illustration of a display screen having an NTSC image ratio or other non-square image ratio displaying an image with padding.

FIG. 8 shows an example of a displayed image 115 with padding 119 in which the displayed image is either of NTSC aspect ratio or of another aspect ratio unequal to one. An operator may use the computer 75 to control the ISC 70 to determine which input modules 20, 23 will pad incoming images.

In many applications, scaling down and padding is preferred to clipping to make up for aspect ratio differences between the input and output videos, because with padding, the entire source image can be seen on the output device 66. With clipping, some of the source image, the clipped portion, is not displayed on the output device 66 and the clipped portion may happen to be a portion that the operator needed to view. Padding 119 may be black to provide a strong contrast with the image 115.

The ISC box 70 is fed by the external computer 75 (FIGS. 2 and 3) that acts as a user interface. An operator may use the computer 75 or user interface to determine whether a full screen will be displayed or whether the picture-in-picture (PIP) feature is to be turned on. PIP allows two different images to be displayed simultaneously on the same video display device 66. One of the images is a background image 123. The other image, typically smaller in scale, is called a window 126. In some embodiments, discussed below, the window 126 covers a portion of the background image 123.

If PIP is turned on, then the operator uses the user interface to determine the source for the PIP background 123, the source for the PIP window 126, and the location where the PIP window 126 will be placed. In embodiments having only quadrants in which the window 126 may be placed, the operator employs the external computer 75 to determine which quadrant the window 126 will be placed in.

An operator can use the foot-pedal 78 (FIG. 2) or other device to switch PIP on and off. Also, the foot-pedal 78 or other device may be used to determine which video source will be the background 123 and which video source will be the window 126. Since all video inputs, regardless of video standard, are synchronous and positioned as desired at the input to the bus 26, PIP is a matter of selecting the desired input video sources. The video images 115 will have already been scaled, if necessary, and the aspect ratio will have been retained by the input module. The register in the input module should indicate one source to be the window 126 and one source to be the background 123. If, for example, SXGA is being employed on the bus 26, and PIP is turned on, then if the image from an input source does not have the SXGA aspect ratio, the input source image can be scaled and padded prior to being placed on the bus 26.

If PIP is turned on, then two different input modules 20, 23 will supply signals to the bus 26, one supplying the background 123 and the other supplying the window 126. The PIP signals then pass through a single output module in embodiments having only a single output module. In embodiments having a plurality of output modules 29, 32, all of the output modules 29, 32 receive the same PIP images from the bus 26 and convert frequencies as appropriate for the respective output devices 66. The PIP images exit all output modules 29, 32 simultaneously. For example, if there are two output modules 29, 32 on a VSC, then both modules receive the same PIP images, however, the images 115 may differ in frequency and resolution if these parameters of the respective output modules 29, 32 differ.

An operator may select the position of the window 126 using the foot-pedal 78 or other control. In one embodiment, for example, the operator is given a choice of four quadrants in the output video in which to place the window. Additionally or alternatively, the input module may be controlled by the ISC 70 in such a way that the window 126 is positioned in places other than quadrants. Also, the window 126 need not be the entire size of a quadrant in which it is placed. Whereas a quadrant is one-quarter of the display screen, a window 126 placed within a quadrant may comprise a portion of the quadrant or the entire quadrant. In the embodiments having quadrants for an operator to choose from, the quadrants correspond to the following output display screen areas: the upper-left quarter, the upper-right quarter, the lower-right quarter, and the lower-left quarter.

Figure 9:
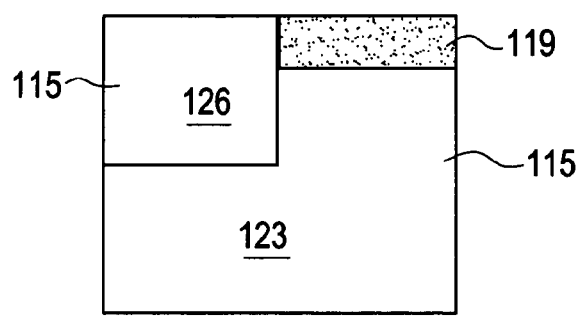
FIG. 9 is a schematic illustration of an embodiment of picture-in-picture in which the background image is an NTSC or other non-square image ratio picture.

When PIP is employed (with input images that have been padded), intelligent positioning of the background source allows operators see a maximum percentage of the background source. If the background video source has an aspect ratio that results in the utilization of padding 119, in some embodiments the ISC 70 instruct the input modules 20, 23 where to position the background 123 away from the quadrant that the operator had selected for window 126 placement. The background video, if padding 119 is present, is positioned by the ISC 70 which instructs the input modules 20, 23 to position the padding 119 to be as far away from the window 126 as possible without the background image 123 being clipped. In this fashion, the window 126 will cover at least a portion of the padding 119, and the amount of the background 123 that is covered by the window 126 is minimized. For example, as seen in FIG. 9, if NTSC is displayed in the background 123 with OEC in the window 126, the NTSC image will be shifted up or down (down in FIG. 9) to minimize image interference. Depending on the size of the background image 123 and the size of the window 126, the window 126 might be on top of a portion of the background image 123 after the background image 123 has been positioned as far from the pre-selected window position as possible without clipping.

Figure 10:
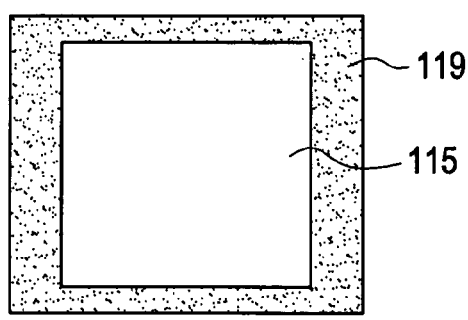
FIG. 10 is a schematic illustration of a non-square display screen having a square aspect ratio image displaying padding around all four sides of the image.

As seen in FIG. 10, some source images have an aspect ratio of one (i.e., the image is a square). In cases of a square image, given some output standards, the displayed image will be a square that is padded on all four sides. In PIP, if the background image 123 has an aspect ratio of one and the output standard is such that the background image 123 would have been padded around all four sides, as seen in FIG. 10, then in some embodiments the ISC 70 instructs the input modules 20, 23 to position the background image 123 toward a corner farthest from the corner contained by a quadrant that the operator had selected for window 126 placement.

Figure 11:
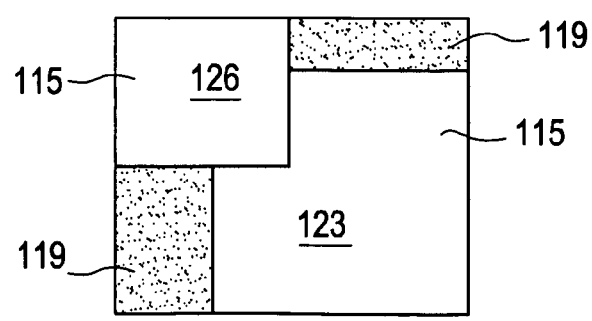
FIG. 11 is a schematic illustration of an embodiment of picture-in-picture in which the background image is square.

FIG. 11 shows an embodiment of PIP in which the upper left quadrant bad been selected by an operator to be the position of the window 126. In FIG. 11, the background 123 is shifted to the lower right quadrant to minimize the amount of background 123 that is covered by the window 126. Padding 119 is around only two sides of the background image 123 in the embodiment of FIG. 11. Padding allows operators to see as much of the background image 123 as possible, because the background 123 is automatically positioned where it will be covered up as little as possible by the window image 126. An example in which padding 119 is all around the background image 123, as shown in FIG. 10, is OEC Hi-Res which has an aspect ratio of one with some black padding 119 all around the image. In a case in which OEC Hi-Res is the background image 123, the image will be moved up or down, and horizontally away from the location of the window 126.

Video standards that may be employed with aspects of the present invention include, but are not limited to the following standards. Inputs may include OEC Hi-Res monochrome input, Dual NTSC/PAL S-Video input, and computer video (VESA standards) input. An output module 29, 32 may be a dual-output module 85 such as a dual SXGA output module or a dual NTSC/PAL S-Video output module. A dual-output module 85 may save some costs, because a dual-output module 85 generally comprises fewer components than two single-output modules 29, 32. HDTV may be used as an input or output standard for input or output modules 29, 32, respectively. Digital standards include digital serial input, digital serial output, and DICOM output. Functionally, DICOM is an output language, but the rest of the standards listed here may be used as inputs and outputs.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A system for converting video standards comprising:
   a first input module receiving first analog video signal from a first video source and converting the first analog video signal to a digital video signal, wherein the first input module converts the first analog video signal from a standard of the first video source to a bus standard;
   a second input module receiving second analog video signal from a second video source and converting the second analog video signal to a digital video signal, wherein the second input module converts the second analog video signal from a standard of the second video source to the bus standard;
   a bus attached to outputs of the first and second input modules;
   an input selection and control device (ISC) for selecting at least one of the first and second input modules to drive the bus;
   first and second output modules attached to an output of the bus;
   a first video device attached to the first output module; and
   wherein the first output module converts a digital video signal from the bus standard to a standard of the first video device.

2. The system of claim 1 wherein at least one of the first and second input modules converts a standard of a video signal to match the video standard of the bus.

3. The system of claim 2 wherein a video standard of the first output module is different from a video standard of the second output module.

4. The system of claim 1 and comprising a computer for controlling the ISC.

5. The system of claim 4 and comprising a foot-pedal for controlling the computer.

6. The system of claim 1 wherein at least one of the input modules is a dual-input module having a pair of connectors connected to sources having identical standards.

7. The system of claim 1 wherein at least one of the output modules is a dual-output module having a pair of connectors connected to two video devices having identical video standards.

8. The system of claim 1 and comprising a third output module, wherein the first, second, and third output modules have different video standards.

9. The system of claim 1 and comprising:
   a second video device; and
   wherein the first video device is attached to the first output module;
   wherein the second video device is attached to the second output module;
   wherein the first and second video devices have different standards.

10. A system for converting video standards comprising:
    a first input module receiving first analog video signal from a first video source and converting the first analog video signal to a digital video signal, wherein the first input module converts the first analog video signal from a standard of the first video source to a bus standard;
    a second input module receiving second analog video signal from a second video source and converting the second analog video signal to a digital video signal, wherein the second input module converts the second analog video signal from a standard of the second video source to the bus standard;
    a bus attached to outputs of the first and second input modules;
    an input selection and control device (ISC) for selecting at least one of the first and second input modules to drive the bus;
    a computer for controlling the ISC;
    first and second output modules attached to an output of the bus;
    a first video device attached to the first output module;
    a second video device attached to the second output module; and
    wherein the first output module converts a standard of a video signal from the bus standard to a standard of the first video device;
    wherein a video standard of the first output module is different from a video standard of the second output module;
    wherein the first and second video devices have different standards.

11. The system of claim 1 wherein the bus standard includes an aspect ratio of a video image.

12. The system of claim 10 wherein the bus standard includes an aspect ratio of a video image.

13. A system for displaying images from two sources, the system comprising:
    a first input module converting a first analog video signal to a first digital video signal, wherein the first input module converts the first analog video signal from a standard of a first video source to a bus standard;
    a second input module converting a second analog video signal to a second digital video signal, wherein the second input module converts the second analog video signal from a standard of a second video source to the bus standard;
    a bus attached to outputs of the first and second input modules;
    a first output module attached to an output of the bus;
    a second output module attached to the output of the bus;
    a first display device attached to one of the first and second output modules; and
    wherein the bus drives the first output module to convert the first and second digital video signals to respective first and second analog display signals containing images for reception by the first display device;

wherein at least a portion of each image from the first and second analog display signals is displayed on the first display device.

14. The system of claim 13 wherein images from one of the first and second analog display signals are displayed in a quadrant of the first display device.

15. The system of claim 13 wherein padding is positioned adjacent at least a portion of an image from the first or second analog video display signals.

16. The system of claim 13 and comprising an ISC for selecting one of the first and second video signals to be a window image and the other video signal to be the background image.

17. The system of claim 13 and comprising:
a third input module attached to the bus.

18. The system of claim 13 and comprising an ISC for controlling positions at which the images from the first and second analog video display signals are displayed on the first display device.

19. The system of claim 13 and comprising:
a second display device; and
wherein the first display device is attached to the first output module;
wherein the second display device is attached to the second output module;
wherein the first and second display devices have different standards.

20. The system of claim 13 wherein the bus standard includes an aspect ratio of a video image.

21. A system for displaying images from two sources, the system comprising:
a first input module converting a first analog video signal to a first digital video signal, wherein the first input module converts the first analog video signal from a standard of a first video source to a bus standard;
a second input module converts a second analog video signal to a second digital video signal, wherein the second input module converts the second analog video signal from a standard of a second video source to the bus standard;
a bus attached to outputs of the first and second input modules;
a first output module attached to an output of the bus;
a second output module attached to an output of the bus;
a first display device attached to the first output module;
a second display device attached to the second output module; and
wherein the first output module converts the first and second digital video signals to respective first and second analog display signals containing images for reception by the first display device;
wherein at least a portion of each image from the first and second analog display signals is displayed on the first display device; and
wherein the first and second display devices have different standards.

22. The system of claim 21 and comprising an ISC for selecting one of the first and second analog video signals to supply window images and the other analog video signal to supply background images.

23. The system of claim 21 wherein the bus standard includes an aspect ratio of a video image.

24. A method for converting a plurality of video sources having a plurality of different standards, the method comprising the steps of:
providing a video standards converter (VSC) comprising:
a first input module;
a second input module;
a bus attached to outputs of the first and second input modules;
a first output module attached to an output of the bus;
a second output module attached to an output of the bus;
employing one of the first and second input modules to convert a video signal from analog to digital, wherein one of the first and second input modules converts a standard of the video signal to a bus standard;
employing the bus to drive one of the first and second output modules to convert the video signal from digital to analog;
selecting one of the first and second input modules to place a video signal onto the bus; and
positioning the video signal as the signal is placed on the bus.

25. The method of claim 24 and comprising the step of providing a third output module attached to the bus.

26. The method of claim 24 and comprising the steps of:
providing a display device attached to one of the output modules; and
displaying images of the video signal on the display device attached to the output module.

* * * * *